United States Patent
Amplatz et al.

(10) Patent No.: US 8,900,287 B2
(45) Date of Patent: Dec. 2, 2014

(54) INTRAVASCULAR DELIVERABLE STENT FOR REINFORCEMENT OF ABDOMINAL AORTIC ANEURYSM

(75) Inventors: Kurt Amplatz, North Oaks, MN (US); John Oslund, Blaine, MN (US); Patrick Russo, Vadnais Heights, MN (US)

(73) Assignee: AGA Medical Corporation, Plymouth, MN (US)

( * ) Notice: Subject to any disclaimer, the term of this patent is extended or adjusted under 35 U.S.C. 154(b) by 1058 days.

(21) Appl. No.: 11/331,640

(22) Filed: Jan. 13, 2006

(65) Prior Publication Data

US 2007/0168018 A1    Jul. 19, 2007

(51) Int. Cl.
*A61F 2/06* (2013.01)
*A61F 2/07* (2013.01)
*A61F 2/90* (2013.01)

(52) U.S. Cl.
CPC ............ *A61F 2/07* (2013.01); *A61F 2002/075* (2013.01); *A61F 2210/0014* (2013.01); *A61F 2250/0015* (2013.01); *A61F 2/90* (2013.01)
USPC ........................................ 623/1.13; 623/1.44

(58) Field of Classification Search
CPC .................................. A61F 2/82; A61F 2/852
USPC ................... 623/1.11, 1.13, 1.15, 1.16, 1.18, 623/1.32–1.34, 1.44, 1.5, 1.51, 1.53
See application file for complete search history.

(56) References Cited

U.S. PATENT DOCUMENTS

| | | |
|---|---|---|
| 4,655,771 A | 4/1987 | Wallsten |
| 4,954,126 A | 9/1990 | Wallsten |
| 5,061,275 A | 10/1991 | Wallsten et al. |
| 5,064,435 A | 11/1991 | Porter |
| 5,084,065 A * | 1/1992 | Weldon et al. ............... 623/1.44 |
| 5,211,658 A * | 5/1993 | Clouse ......................... 623/1.14 |
| 5,360,443 A * | 11/1994 | Barone et al. ................ 623/1.13 |
| 5,366,504 A | 11/1994 | Andersen et al. |
| 5,383,925 A | 1/1995 | Schmitt |
| 5,464,449 A * | 11/1995 | Ryan et al. ................... 623/1.23 |
| 5,476,508 A | 12/1995 | Amstrup |
| 5,549,663 A * | 8/1996 | Cottone, Jr. .................. 623/1.22 |
| 5,571,173 A * | 11/1996 | Parodi ........................... 623/1.13 |

(Continued)

FOREIGN PATENT DOCUMENTS

| | | |
|---|---|---|
| EP | 1477134 | 11/2004 |
| EP | 1645246 | 4/2006 |
| WO | WO/02/055125 | 7/2002 |

*Primary Examiner* — Dianne Dornbusch
(74) *Attorney, Agent, or Firm* — Armstrong Teasdale LLP

(57) ABSTRACT

A stent/graft especially designed to be used in a minimally invasive surgical procedure for treating an abdominal aortic aneurysm (AAA) comprises an innermost tubular structure of a length ($L_1$) formed by braiding a relatively few strands of shape memory alloy wire. The pick and pitch of the braid are such as to provide relative large fenestrations in the tubular wall. A portion of the innermost tubular structure of a length $L_2<L_1$ is surrounded by a further braided tubular structure having relatively many strands that occlude the fenestrations of the innermost tubular structure. The composite structure can be stretched to reduce the outer diameter of the stent/graft, allowing it to be drawn into a lumen of a delivery catheter. The catheter can then be advanced through the vascular system to the site of the AAA and then ejected, allowing it to self-expand with the portion $L_2$ bridging the aneurysm. The portion $L_1>L_2$ does not block blood flow to the renal arteries while the portion $L_2$ prevents the aneurysm to grown and burst.

12 Claims, 1 Drawing Sheet

(56) References Cited

U.S. PATENT DOCUMENTS

| | | | | |
|---|---|---|---|---|
| 5,628,788 | A * | 5/1997 | Pinchuk | 623/1.2 |
| 5,639,278 | A * | 6/1997 | Dereume et al. | 623/1.13 |
| 5,645,559 | A * | 7/1997 | Hachtman et al. | 623/1.2 |
| 5,665,117 | A * | 9/1997 | Rhodes | 623/1.1 |
| 5,667,523 | A * | 9/1997 | Bynon et al. | 623/1.13 |
| 5,676,697 | A * | 10/1997 | McDonald | 623/1.35 |
| 5,681,346 | A * | 10/1997 | Orth et al. | 606/198 |
| 5,693,085 | A * | 12/1997 | Buirge et al. | 623/1.13 |
| 5,728,131 | A * | 3/1998 | Frantzen et al. | 623/1.13 |
| 5,741,325 | A * | 4/1998 | Chaikof et al. | 623/1.35 |
| 5,755,773 | A * | 5/1998 | Evans et al. | 606/194 |
| 5,769,882 | A * | 6/1998 | Fogarty et al. | 128/898 |
| 5,769,884 | A * | 6/1998 | Solovay | 623/1.13 |
| 5,788,626 | A * | 8/1998 | Thompson | 623/1.15 |
| 5,800,508 | A | 9/1998 | Goicoechea et al. | |
| 5,824,043 | A * | 10/1998 | Cottone, Jr. | 623/1.13 |
| 5,843,167 | A * | 12/1998 | Dwyer et al. | 623/1.14 |
| 5,906,641 | A * | 5/1999 | Thompson et al. | 623/1.15 |
| 5,916,264 | A * | 6/1999 | Von Oepen et al. | 623/1.15 |
| 6,102,938 | A * | 8/2000 | Evans et al. | 623/1.35 |
| 6,102,940 | A * | 8/2000 | Robichon et al. | 623/1.35 |
| 6,110,198 | A | 8/2000 | Fogarty et al. | |
| 6,129,756 | A | 10/2000 | Kugler et al. | |
| 6,152,956 | A | 11/2000 | Pierce | |
| 6,156,064 | A * | 12/2000 | Chouinard | 623/1.44 |
| 6,162,246 | A * | 12/2000 | Barone | 623/1.35 |
| 6,168,619 | B1 * | 1/2001 | Dinh et al. | 623/1.13 |
| 6,287,335 | B1 * | 9/2001 | Drasler et al. | 623/1.28 |
| 6,312,458 | B1 | 11/2001 | Golds | |
| 6,342,068 | B1 | 1/2002 | Thompson | |
| 6,344,052 | B1 | 2/2002 | Greenan et al. | |
| 6,488,705 | B2 | 12/2002 | Schmitt et al. | |
| 6,585,758 | B1 | 7/2003 | Chouinard et al. | |
| 6,626,939 | B1 * | 9/2003 | Burnside et al. | 623/1.38 |
| 6,669,720 | B1 * | 12/2003 | Pierce | 623/1.13 |
| 6,695,875 | B2 | 2/2004 | Stelter et al. | |
| 6,709,451 | B1 | 3/2004 | Noble et al. | |
| 6,709,455 | B1 | 3/2004 | Chouinard et al. | |
| 6,860,900 | B2 | 3/2005 | Clerc et al. | |
| 6,932,837 | B2 | 8/2005 | Amplatz et al. | |
| 7,083,822 | B2 * | 8/2006 | Brightbill | 427/2.25 |
| 7,108,716 | B2 | 9/2006 | Burnside et al. | |
| 2001/0049554 | A1 * | 12/2001 | Ruiz et al. | 623/1.44 |
| 2002/0052643 | A1 | 5/2002 | Wholey et al. | |
| 2002/0052645 | A1 | 5/2002 | Kugler et al. | |
| 2002/0143384 | A1 * | 10/2002 | Ozasa | 623/1.12 |
| 2003/0023299 | A1 * | 1/2003 | Amplatz et al. | 623/1.13 |
| 2003/0074055 | A1 * | 4/2003 | Haverkost | 623/1.16 |
| 2003/0130724 | A1 * | 7/2003 | DePalma et al. | 623/1.16 |
| 2003/0149473 | A1 | 8/2003 | Chouinard et al. | |
| 2004/0010307 | A1 * | 1/2004 | Grad et al. | 623/1.15 |
| 2004/0010308 | A1 * | 1/2004 | Zafrir-Pachter et al. | 623/1.35 |
| 2004/0044396 | A1 * | 3/2004 | Clerc et al. | 623/1.13 |
| 2004/0059406 | A1 | 3/2004 | Cully et al. | |
| 2004/0098095 | A1 * | 5/2004 | Burnside et al. | 623/1.13 |
| 2004/0162606 | A1 | 8/2004 | Thompson | |
| 2004/0193245 | A1 | 9/2004 | Deem et al. | |
| 2004/0215318 | A1 * | 10/2004 | Kwitkin | 623/1.13 |
| 2004/0254628 | A1 * | 12/2004 | Nazzaro et al. | 623/1.13 |
| 2005/0033405 | A1 | 2/2005 | Solovay | |
| 2005/0197687 | A1 * | 9/2005 | Molaei et al. | 623/1.2 |
| 2005/0197690 | A1 * | 9/2005 | Molaei et al. | 623/1.13 |
| 2005/0267568 | A1 | 12/2005 | Berez et al. | |
| 2006/0020329 | A1 * | 1/2006 | Raze et al. | 623/1.42 |
| 2006/0095112 | A1 * | 5/2006 | Jones | 623/1.15 |

* cited by examiner

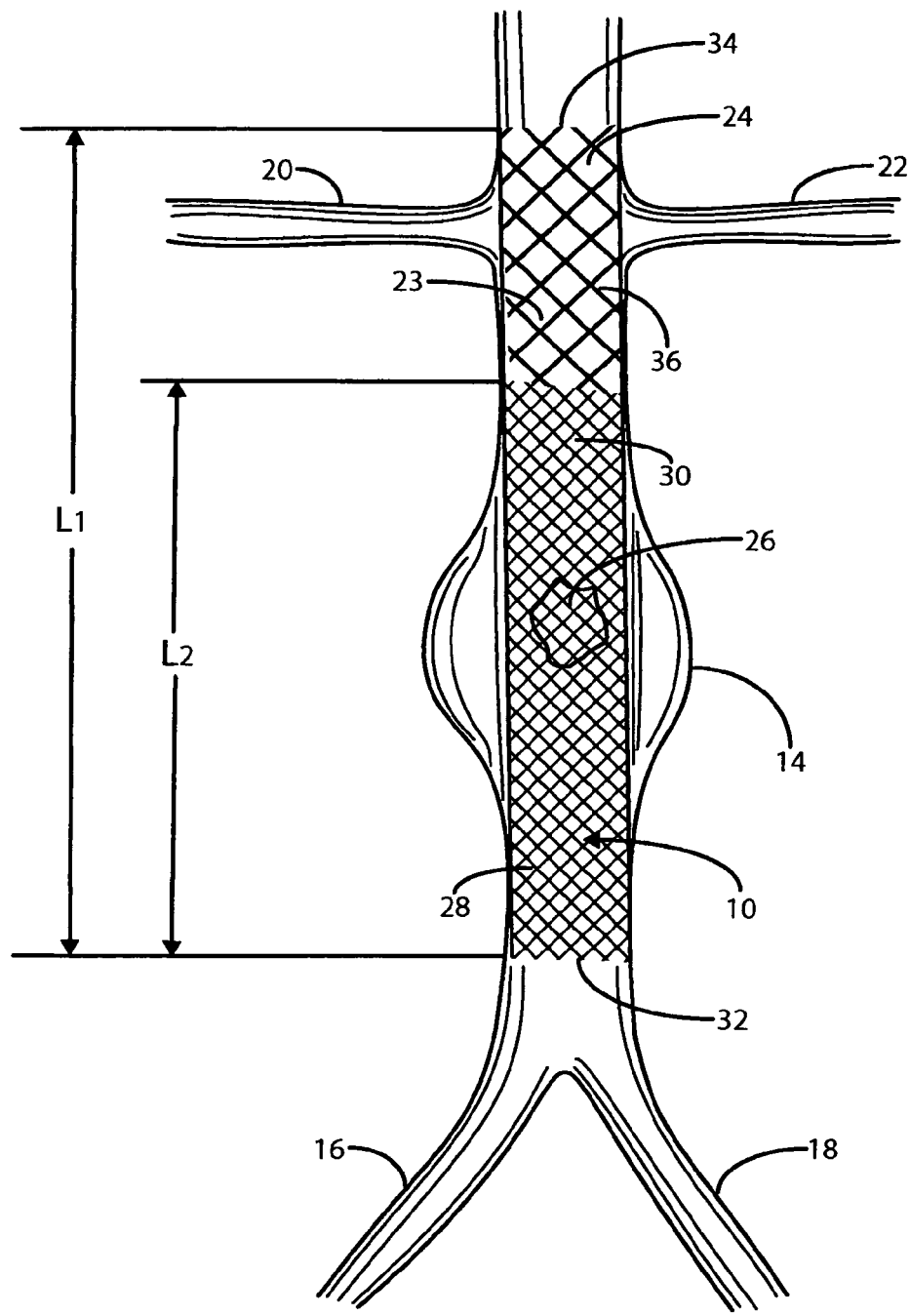

INTRAVASCULAR DELIVERABLE STENT FOR REINFORCEMENT OF ABDOMINAL AORTIC ANEURYSM

BACKGROUND OF THE INVENTION

I. Field of the Invention

This invention relates generally to an intravascular deliverable stent for reinforcing a blood vessel, and more particularly to such a stent specifically designed for addressing an abdominal aortic aneurysm (AAA).

II. Discussion of the Prior Art

An aortic aneurysm is a weak area in the aorta, the main blood vessel that carries blood from the heart to the rest of the body. The aorta extends upwards from the heart in the chest and then arches downwards, traveling through the chest (the thoracic aorta) and into the abdomen (the abdominal aorta). The normal diameter of the abdominal aorta is about one inch. As blood flows through the aorta, the weak area bulges like a balloon and can burst if the balloon gets too big.

Most commonly, aortic aneurysms occur in the portion of the vessel below the renal artery origins. The aneurysm may extend into the vessel's supplying the hips and pelvis.

Once an aneurysm reaches 5 cm in diameter, it is usually considered necessary to treat to prevent rupture. Below 5 cm, the risk of the aneurysm rupturing is lower than the risk of conventional surgery in patients with normal surgical risks. The goal of therapy for aneurysms is to prevent them from rupturing. Once an AAA has ruptured, the chances of survival are low, with 80-90 percent of all ruptured aneurysms resulting in death. These deaths can be avoided if the aneurysm is detected and treated before it ruptures.

Most aortic aneurysms occur in the abdominal aorta, the main cause being arteriosclerosis. This is a condition in which fatty deposits are laid down in the walls of the arteries, which are less elastic and weaker as a result. Major risk factors for arteriosclerosis are smoking and high blood pressure as well as genetic factors.

AAA can be diagnosed from their symptoms when they occur, but this is often too late. They are usually found on routine physical examination and chest and abdominal X-rays. On examination, a doctor may feel a pulsating mass in the abdomen. If the doctor suspects an aneurysm, he/she will probably request that an ultrasound scan be carried out. Other scans, such as computerized tomography (CT) and magnetic resonance imaging (MRI) may also be performed. These scanning techniques are very useful for determining the exact position of the aneurysm.

The surgical procedure for treating AAA involves replacing the affected portion of the aorta with a synthetic graft, usually comprising a tube made out of an elastic material with properties very similar to that of a normal, healthy aorta. This major operation is usually quite successful with a mortality of between 2 and 5 percent. The risk of death from a ruptured AAA is about 50%, even during surgery.

More recently, instead of performing open surgery in undertaking aneurysm repair, vascular surgeons have installed an endovascular stent/graft delivered to the site of the aneurysm using elongated catheters that are threaded through the patient's blood vessels. Typically, the surgeon will make a small incision in the patient groin area and then insert a delivery catheter containing a collapsed, self-expanding or balloon-expandable stent/graft to a location bridging the aneurysm, at which point the stent/graft is delivered out from the distal end of the delivery catheter and allowed or made to expand to approximately the normal diameter of the aorta at that location. The stent/graft, of course, is a tubular structure allowing blood flow through the lumen thereof and removing pressure from the aneurysm. Over time, the stent/graft becomes endothelialized and the space between the outer wall of the stent and the aneurysm ultimate fills with clotted blood. At this time, the aneurysm is no longer subjected to aortic pressures and thus will not continue to grow.

In treating AAA, it is important that the stent be accurately placed so as not to occlude blood flow through the renal arteries which branch off from the abdominal aorta.

In the Amplatz et al. U.S. Pat. No. 6,932,837, there is described a collapsible stent/graft designed for grafting a lumen of a selected blood vessel or other tubular organ. The stent/graft comprises a woven or braided fabric made from a plurality of strands of a shape memory alloy. The fabric is formed as a tube and each end of the device is open to allow fluid flow therethrough. The device can be longitudinally stretched to thereby reduce its diameter, allowing it to be inserted within the lumen of a delivery catheter. When ejected from the distal end of the delivery catheter, the stent/graft will self-expand to a predetermined outer diameter sufficient to engage the wall of the tubular vessel being treated.

While the device in the '837 patent is altogether suitable for use as a coronary stent, it is not well suited for the intravascular treatment of AAA. That device is of a uniform weave, but necessarily is of a wire density that is insufficient to limit the exposure of the aneurysm to aortic blood pressure. Should this stent/graft also encroach upon the ostia of the renal arteries, it will necessarily unduly restrict blood flow to the kidneys.

A need, therefore, exists for a stent/graft that can be placed using an endovascular approach in the treatment of AAA, but that will not unduly occlude blood flow to the kidneys. The present invention provides such a device.

SUMMARY OF THE INVENTION

The present invention provides a catheter-deliverable, endovascular stent for treating AAA that comprises an innermost tubular structure having a first length. It comprises a plurality of braided wire strands of a shape memory alloy. The pick and pitch of the braid is chosen to define openings sufficiently large so as to not materially impede blood flow through the wall of the innermost tubular structure. Surrounding the innermost tubular structure is at least one further tubular structure of a predetermined diameter, but having a length that is less than the length of the innermost tubular structure. The further tubular structure also comprises a plurality of braided wire strands that are greater in number than the number of strands making up the innermost tubular structure. The wire strands of the further braided tubular structure also comprise a shape memory alloy and the braid thereof has a pick and pitch which define openings sufficiently small so as to substantially preclude blood flow therethrough. Longitudinal stretching of the coaxially disposed innermost and further tubular structures reduces the outer diameter of the device sufficiently to permit it to be loaded into the lumen of an endovascular delivery catheter. The release of the stent from the delivery catheter allows its outer diameter to expand back to its original predetermined diameter as limited by the wall of the aorta.

The portion of the innermost tubular structure that extends beyond a distal terminus of the further tubular structure can overlay the juncture of the patient's renal arteries with his/her abdominal aorta when the further tubular structure bridges an abdominal aortic aneurysm, but without blocking blood flow to the kidneys.

DESCRIPTION OF THE DRAWINGS

The foregoing features, objects and advantages of the invention will become apparent to those skilled in the art from the following detailed description of a preferred embodiment, especially when considered in conjunction with the accompanying drawing in which:

FIG. 1 is a side elevation view of the stent/graft of the present invention disposed in a patient's abdominal aorta so as to bridge an aneurysm, the abdominal aorta being shown in sectional view so as not to obscure the stent/graft.

DESCRIPTION OF THE PREFERRED EMBODIMENT

Referring to FIG. 1, there is indicated generally by numeral 10 the preferred embodiment of the stent/graft constructed in accordance with the present invention. The stent/graft 10 is shown in place in a segment of the abdominal aorta 12 having an aneurysm 14. At its lower end, the abdominal aorta 12 branches into the left and right common iliac arteries 16 and 18. Also shown in FIG. 1 are renal arteries 20 and 22 leading to the kidneys (not shown).

The stent/graft 10 comprises an innermost tubular structure 23 of a first length ($L_1$). The innermost tubular structure comprises a first plurality of braided wire strands 24, preferably of a shape memory alloy. The braid comprising the innermost tubular structure 23 has a predetermined pick and pitch to define openings through the structure that are sufficiently large so as not to materially impede blood flow through its fenestrated wall. The wire strands may have a diameter in a range of from 0.002 to 0.010 inch and tubular structure 23 is designed to provide an adequate radial outward force necessary for self-expansion of the stent/graft 10.

At least one further tubular structure 26 of a predetermined diameter is placed in coaxial surrounding relationship with a predetermined length portion ($L_2$) of the innermost tubular structure where the further tubular structure 26 is of a lesser length than that of the innermost tubular structure 23.

The further tubular structure surrounding the innermost tubular structure is comprised of a second plurality of braided wire strands 28 that is significantly greater in number than the first plurality of braided wire strands making up the innermost tubular structure. The strands 28 are also of a shape memory alloy and they are braided so as to have a pick and pitch to define openings sufficiently small so as to substantially preclude blood flow through the wall thereof.

Without limitation, the innermost tubular structure 23 may comprise 36 strands of 0.005 diameter wire woven so as to exhibit fenestrations with an area of about 0.0016 (0.040× 0.040 inch square) sq. in. The further tubular structure 26 may then comprise 144 wires formed of a shape memory alloy, such as Nitinol, that are braided so as define significantly smaller fenestrations that are sufficiently small so as to substantially preclude blood flow through the portion of the stent/graft 10 of the length $L_2$.

In accordance with the present invention, even smaller fenestrations can be provided over the length $L_2$ by having a second, outermost, tubular braided structure 30 coaxially surrounding the intermediate tubular structure 26 that surrounds the innermost tubular structure 23. This second and outermost tubular structure 30 would also extend the length $L_2$ and may be identical in its braided configuration to the further tubular structure 26, e.g., 144 strands of 0.001 diameter Nitinol wire braided so as to have 0.0001 (0.010×0.010) sq. in. openings.

It is contemplated that the stent/graft 10 be fabricated using the method set out in U.S. Pat. No. 6,123,715 to Curtis Amplatz, the teachings of which are hereby incorporated by reference. The innermost structure 23 could be braided to form a tubular fabric as would the further tubular structure or structures 26. The outer braided tube or tubes would then be concentrically disposed over the innermost tubular structure and the combination would be placed about a cylindrical mandrel of the desired outer diameter for the stent/graft. This assembly would then be heated to a predetermined temperature and for a length of time sufficient to heat set the tubular structures to the diameter of the mandrel. The opposite free ends 32, 34 of the strands comprising the innermost tubular structure 23 may be flared radially outward by 10° to 30° to provide improved apposition with the inner wall of the aorta. Following removal from the mold, the two or more coaxial braided tubes may be held together with a few polyester suture stitches.

In use, the thus-formed stent would be releasably affixed at its proximal end to a pusher catheter in the manner described in the copending Amplatz patent application Ser. No. 11/121, 386, filed May 4, 2005 and entitled "System for the Controlled Delivery of Stents and Grafts". The stent would then be drawn into a lumen of an intravascular delivery catheter. The delivery catheter would be introduced into the patient using the well-known Seldinger technique and then threaded through the vascular system until a distal end of the delivery catheter is proximate an aneurysm to be treated. With the stent and the pusher catheter held stationary, the delivery catheter is drawn in the proximal direction to eject the stent from the distal end of the delivery catheter where the stent then self-expands to engage the aortic wall with the portion of length $L_2$ in FIG. 1 bridging the aneurysm being treated. The portion of the innermost tubular structure that extends beyond the distal end of the further tubular structure may overlay the ostia of the renal arteries 20 and 22. However, because of the open weave construction of that portion of the inner tubular structure, it does not significantly impede blood flow through the renal arteries or create a stenosis. The added length of the stent/graft 10 provided by the extension of the innermost tubular structure 23 beyond the distal end of the further layer (s) 26, 30 serves to better stabilize the stent/graft within the abdominal aorta, preventing its displacement before endotheliozation can occur.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A catheter deliverable stent for treating an abdominal aortic aneurysm comprising:

a continuous innermost tubular structure having a first length and comprising a first plurality of braided strands forming a first braid comprising a first shape memory alloy, the first braid of the continuous innermost tubular structure having a predetermined pick and pitch to define openings sufficiently large so as to not materially impede blood flow therethrough, the first braid extending from a first end of the innermost tubular structure to a second end of the innermost tubular structure;

a continuous outer tubular structure having a second length less than the first length and comprising a second plurality of braided strands forming a second braid comprising a second shape memory alloy, the second braid of the continuous outer tubular structure having a predetermined pick and pitch to define openings sufficiently small so as to substantially preclude blood flow therethrough, the continuous outer tubular structure being in a coaxial relationship with and surrounding the continuous innermost tubular structure, wherein the continuous innermost tubular structure and the continuous outer tubular structure are both adapted to self expand and together form a composite tubular structure having a predetermined diameter;

wherein a longitudinal stretching of the composite tubular structure reduces the outer diameter of the composite tubular structure sufficiently to allow the composite tubular structure to be loaded into a lumen of an intravascular delivery catheter, and wherein release of the composite tubular structure from the intravascular delivery catheter allows the composite tubular structure to self expand back to said predetermined diameter.

2. The catheter deliverable stent according to claim 1, wherein a portion of the continuous innermost tubular structure extending beyond a terminus of the continuous outer tubular structure is adapted to overlay the juncture of a patient's renal arteries within the patient's abdominal aorta when the continuous outer tubular structure bridges an abdominal aortic aneurysm.

3. The catheter deliverable stent according to claim 1, further comprising an additional outermost tubular structure placed in a generally coaxial surrounding relationship with the continuous outer tubular structure along at least a length portion thereof.

4. The catheter deliverable stent according to claim 3, wherein the additional outermost tubular structure and the continuous outer tubular structure each respectively comprise 144 braided wire strands.

5. The catheter deliverable stent according to claim 3, wherein the outermost tubular structure comprises a third plurality of braided strands forming a third braid, the third braid having a predetermined pick and pitch to define openings sufficiently small so as to substantially preclude blood flow therethrough.

6. The catheter deliverable stent according to claim 5, wherein the second braid and the third braid define openings equal in area.

7. The catheter deliverable stent according to claim 1, wherein the first braid comprising said plurality of braided strands comprises 36 wire strands and the second braid comprising said plurality of braided strands comprises 144 wire strands.

8. The catheter deliverable stent according to claim 1, wherein the continuous innermost tubular structure is flared outward.

9. The catheter deliverable stent according to claim 1, wherein the first braid defines openings having an area of about 0.0016 square inches and the second braid defines openings having an area of about 0.0001 square inches.

10. The catheter deliverable stent according to claim 1, wherein the continuous innermost tubular structure comprises wires having a diameter of from 0.002-0.010 inch and the continuous outer tubular structure comprises wires having a diameter of about 0.001 inch.

11. The catheter deliverable stent according to claim 1, wherein the first shape memory alloy is the same as the second shape memory alloy.

12. A catheter deliverable stent for treating an abdominal aortic aneurysm comprising:

an innermost tubular structure having a first length, first and second ends and comprised of a first plurality of braided strands of a shape memory alloy, wherein the innermost tubular structure has a predetermined pick and pitch extending from the first to the second end and defining openings across the entire first length having an area sufficiently large so as to not materially impede blood flow therethrough;

an outer tubular structure having a second length shorter than the first length, first and second ends, and comprised of a second plurality of braided strands of a shape memory alloy, wherein the outer tubular structure has a predetermined pick and pitch to define openings having an area sufficiently small so as to substantially preclude blood flow therethrough;

the innermost tubular structure and the outer tubular structure each having a preset expanded diameter and being self expandable from a compressed diameter to the preset expanded diameter, the innermost tubular structure surrounded by and coaxial with the outer tubular structure to form a composite tubular structure; and wherein a longitudinal stretching of the composite tubular structure reduces the outer diameter of the composite tubular structure sufficiently to allow the structure to be loaded into a lumen of an intravascular delivery catheter, and wherein release of the composite tubular structure from the catheter allows the structure to self expand back to said predetermined diameter.

* * * * *